United States Patent
Wu et al.

(10) Patent No.: US 12,313,616 B2
(45) Date of Patent: May 27, 2025

(54) SOLUTION DETECTOR

(71) Applicant: InnoLux Corporation, Miao-Li County (TW)

(72) Inventors: Fuh-Tsang Wu, Miao-Li County (TW); Wen-Hsiang Liao, Miao-Li County (TW)

(73) Assignee: INNOLUX CORPORATION, Chu-Nan (TW)

( * ) Notice: Subject to any disclaimer, the term of this patent is extended or adjusted under 35 U.S.C. 154(b) by 1131 days.

(21) Appl. No.: 17/182,738

(22) Filed: Feb. 23, 2021

(65) Prior Publication Data
US 2021/0278346 A1    Sep. 9, 2021

(30) Foreign Application Priority Data

Mar. 5, 2020  (TW) .................. 109107315

(51) Int. Cl.
*G01N 33/18*    (2006.01)
*G01N 27/416*   (2006.01)

(52) U.S. Cl.
CPC ......... *G01N 33/18* (2013.01); *G01N 27/4167* (2013.01)

(58) Field of Classification Search
CPC .... G01N 21/80; G01N 33/18; G01N 33/1813; G01N 27/07; G01N 27/126; G01N 27/4035; G01N 27/4148; G01N 27/414; G01N 27/00; G01N 27/4167; G01N 31/221; G01N 21/31
See application file for complete search history.

(56) References Cited

U.S. PATENT DOCUMENTS

| | | | | |
|---|---|---|---|---|
| 10,038,022 B1* | 7/2018 | Chen | ................ | H01L 27/14623 |
| 2017/0010238 A1* | 1/2017 | Johnson | ................. | G01N 27/34 |
| 2018/0364194 A1* | 12/2018 | Lee | ........................ | H01L 29/458 |
| 2019/0025273 A1* | 1/2019 | Brondum | ........... | G01N 27/4165 |
| 2019/0369044 A1* | 12/2019 | Chang | ................ | G01N 27/4146 |

FOREIGN PATENT DOCUMENTS

| | | | |
|---|---|---|---|
| KR | 101990793 | * | 6/2019 |
| TW | I667472 B | | 8/2019 |

OTHER PUBLICATIONS

English Espacenet Machine Translation of KR101990793B1. (Year: 2019).*

* cited by examiner

*Primary Examiner* — Kathryn Elizabeth Limbaugh
(74) *Attorney, Agent, or Firm* — MUNCY, GEISSLER, OLDS & LOWE, P.C.

(57) ABSTRACT

A solution detector is provided, which includes: a substrate; a first light detecting element disposed on the substrate and including a first transistor; and a pH value sensing module disposed on the substrate and including a working electrode and a reference electrode.

17 Claims, 6 Drawing Sheets

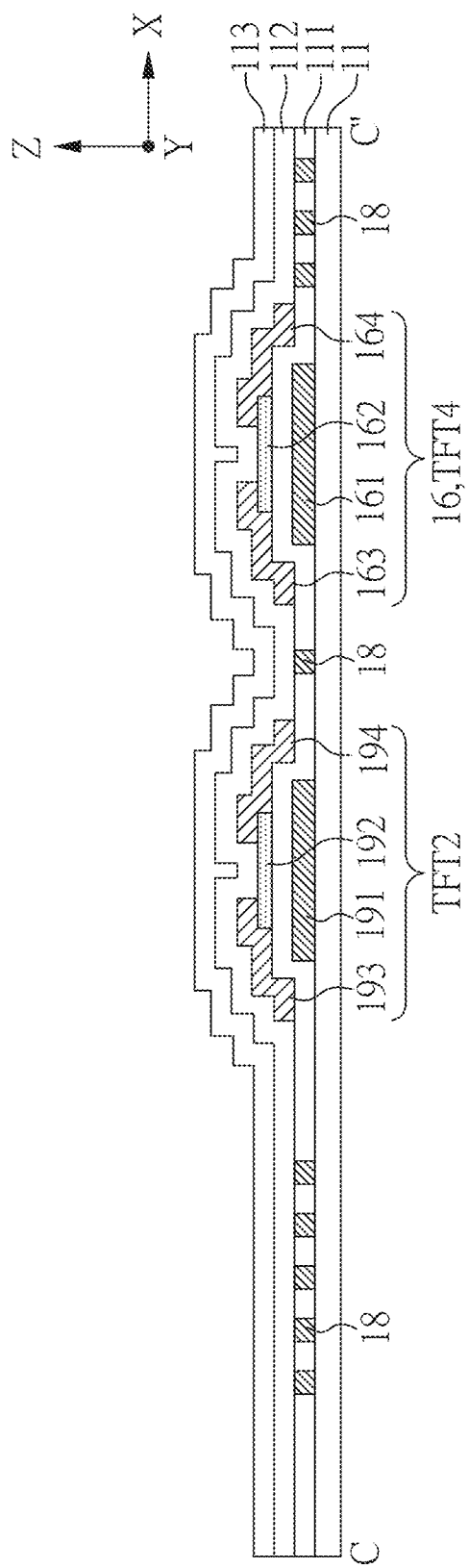
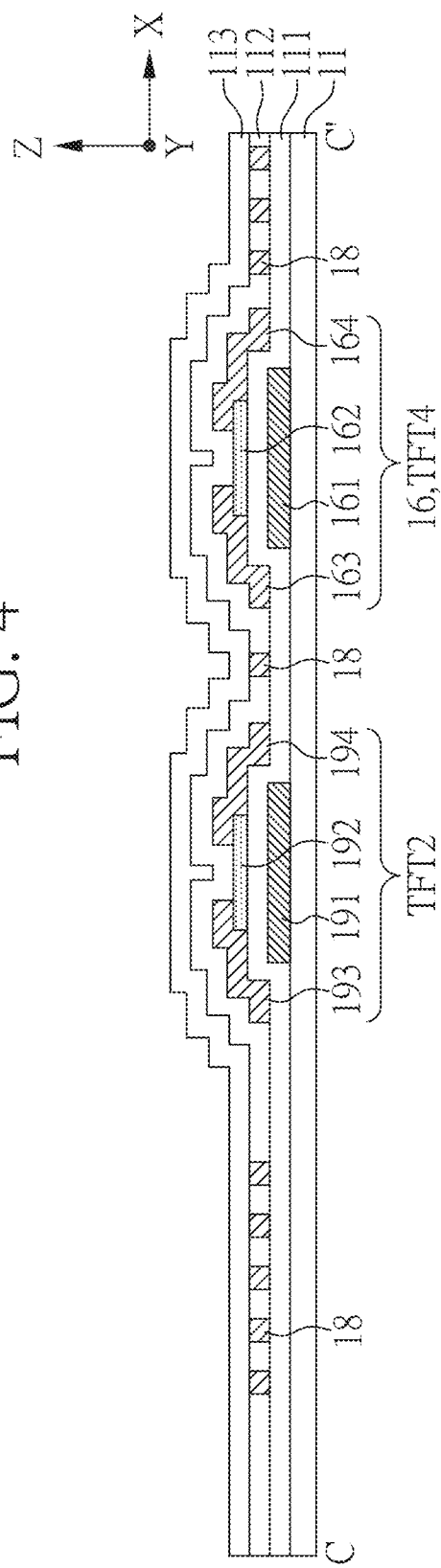
FIG. 4
FIG. 5

SOLUTION DETECTOR

CROSS REFERENCE TO RELATED APPLICATION

This application claims the benefits of the Taiwan Patent Application Serial Number 109107315, filed on Mar. 5, 2020, the subject matter of which is incorporated herein by reference.

BACKGROUND

1. Field

The present disclosure relates to a solution detector. More particularly, the present disclosure relates to a solution detector with a transistor.

2. Description of Related Art

Conventional industrial water detection is mainly performed by a pH value sensing device with glass electrodes, which has a wide pH detection range and good operation stability but is expensive. In addition, when the glass electrodes are not used, they have to be immersed into an electrolyte solution to maintain their activity, so the storage thereof is not convenient. On the other hand, the domestic pH detection is usually performed by pH universal indicator papers. Although the pH universal indicator papers have the advantages of low cost and easy use, the sensitivity thereof is low. In addition, the detection of the pH universal indicator papers is performed by color changes, so the detection results cannot be quantified and stored. Furthermore, the detection of the pH universal indicator papers is judged by naked eyes, and the detection errors may easily occur.

Therefore, it is desirable to provide a solution detector with the advantages of low cost, high stability and easy operation to expand the applications of the solution detector.

SUMMARY

The present disclosure provides a solution detector, comprising: a substrate; a first light detecting element disposed on the substrate and comprising a first transistor; and a pH value sensing module disposed on the substrate and comprising a working electrode and a reference electrode.

Other novel features of the disclosure will become more apparent from the following detailed description when taken in conjunction with the accompanying drawings.

BRIEF DESCRIPTION OF THE DRAWINGS

FIG. 4 is a cross-sectional schematic view of FIG. 1 along a line C-C'.

FIG. 5 is a cross-sectional schematic view of FIG. 1 along a line C-C' according to another embodiment of the present disclosure.

DETAILED DESCRIPTION OF EMBODIMENT

Figure 1:
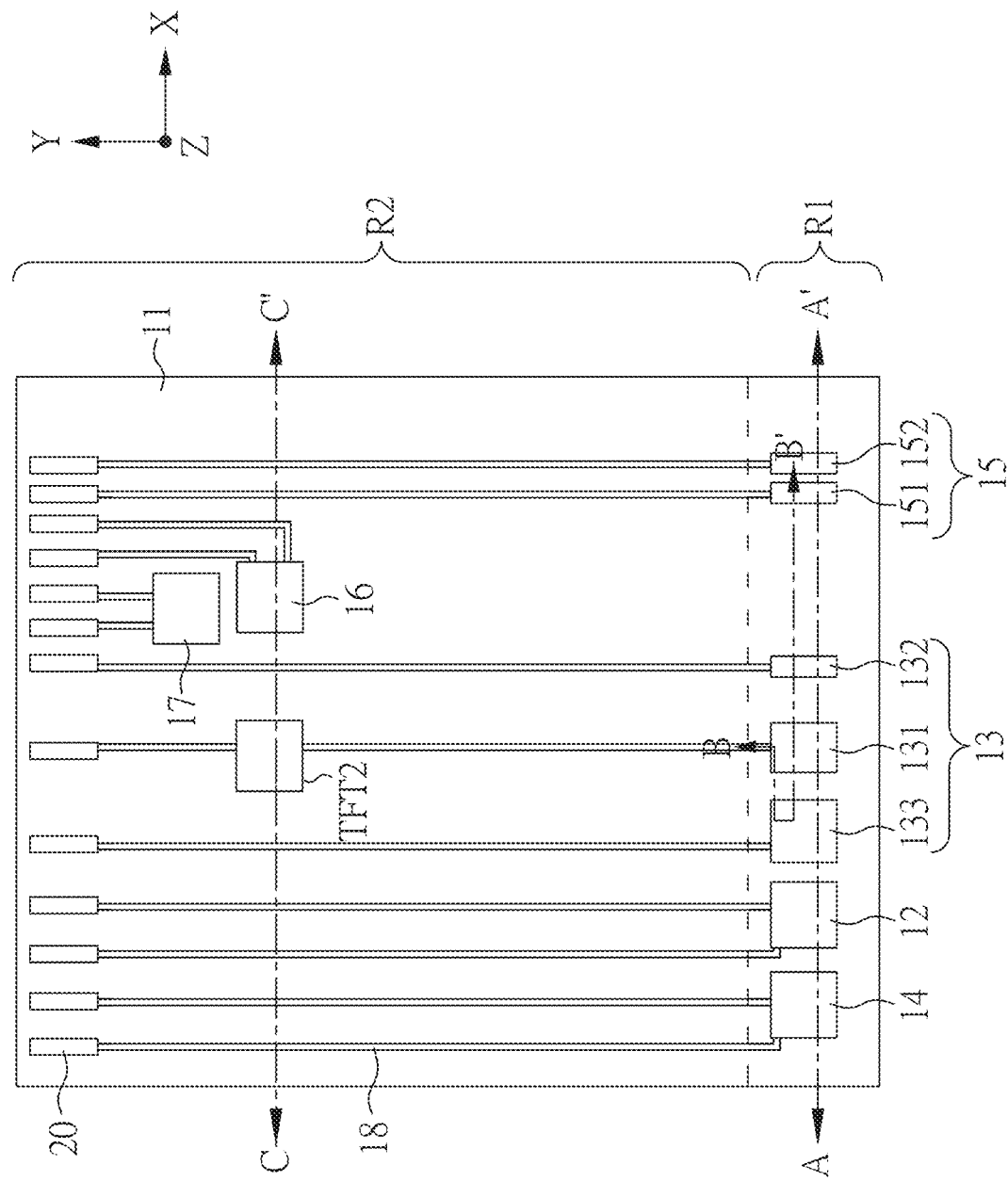
FIG. 1 is a top schematic view of a solution detector according to one embodiment of the present disclosure.

Different embodiments of the present disclosure are provided in the following description. These embodiments are meant to explain the technical content of the present disclosure, but not meant to limit the scope of the present disclosure. A feature described in an embodiment may be applied to other embodiments by suitable modification, substitution, combination, or separation.

It should be noted that, in the present specification, when a component is described to comprise an element, it means that the component may comprise one or more of the elements, and it does not mean that the component has only one of the element, except otherwise specified.

Moreover, in the present specification, the ordinal numbers, such as "first" or "second", are used to distinguish a plurality of elements having the same name, and it does not means that there is essentially a level, a rank, an executing order, or an manufacturing order among the elements, except otherwise specified. A "first" element and a "second" element may exist together in the same component, or alternatively, they may exist in different components, respectively. The existence of an element described by a greater ordinal number does not essentially means the existence of another element described by a smaller ordinal number.

In the present specification, except otherwise specified, the feature A "or" or "and/or" the feature B means the existence of the feature A, the existence of the feature B, or the existence of both the features A and B. The feature A "and" the feature B means the existence of both the features A and B. The term "comprise(s)", "comprising", "include(s)", "including", "have", "has" and "having" means "comprise(s)/comprising but is/are/being not limited to".

Moreover, in the present specification, the terms, such as "top", "upper", "bottom", "front", "back", or "middle", as well as the terms, such as "on", "above", "over", "under", "below", or "between", are used to describe the relative positions among a plurality of elements, and the described relative positions may be interpreted to include their translation, rotation, or reflection.

Furthermore, the terms recited in the specification and the claims such as "above", "over", or "on" are intended not only directly contact with the other element, but also intended indirectly contact with the other element. Similarly, the terms recited in the specification and the claims such as "below", or "under" are intended not only directly contact with the other element but also intended indirectly contact with the other element.

Furthermore, the terms recited in the specification and the claims such as "connect" is intended not only directly connect with other element, but also intended indirectly connect and electrically connect with other element.

Furthermore, when a value is in a range from a first value to a second value, the value can be the first value, the second value, or another value between the first value and the second value.

Moreover, in the present specification, a value may be interpreted to cover a range within ±20% of the value, and in particular, a range within ±10%, ±5%, ±3%, ±2%, ±1% or ±0.5% of the value, except otherwise specified. The value provided in the present specification is an approximate value, which means the meaning "about" is also included in the present disclosure without specifically specifying "about".

In the present specification, except otherwise specified, the terms (including technical and scientific terms) used herein have the meanings generally known by a person skilled in the art. It should be noted that, except otherwise specified in the embodiments of the present disclosure, these terms (for example, the terms defined in the generally used dictionary) should have the meanings identical to those known in the art, the background of the present disclosure or the context of the present specification, and should not be read by an ideal or over-formal way.

FIG. 1 is a top schematic view of a solution detector according to one embodiment of the present disclosure. As shown in FIG. 1, the solution detector of the present embodiment comprises: a substrate 11; a first light detecting element 12 disposed on the substrate 11 and comprising a first transistor (not shown in the figure); and a pH value sensing module 13 disposed on the substrate 11 and comprising a working electrode 131 and a reference electrode 132. The working electrode 131 is electrically connected to a second transistor TFT2. In addition, the pH value sensing module 13 may selectively comprise a counter electrode 133.

Even not shown in the figure, in the solution detector of the present embodiment, a mark may be selectively disposed on the corner of the substrate 11. For example, when a mother substrate is used to prepare the solution detector of the present embodiment, the elements of plural solution detectors can be simultaneously formed on the mother substrate, and the solution detector of the present embodiment can be obtained after cutting the mother substrate. In this case, the mark can be used as an alignment indicator for cutting.

Even not shown in the figure, in the solution detector of the present embodiment, the region of the substrate 11 without disposing elements thereon may be selectively disposed with other elements, such as verniers, bar codes or other elements. Examples of the bar codes may include, but are not limited to 1D bar code or 2D bar bode (for example, QR code).

As shown in FIG. 1, the solution detector of the present embodiment may further selectively comprise a first temperature sensing unit 14 disposed on the substrate 11. In addition, the solution detector of the present embodiment may further selectively comprise an electrical conductivity sensing module 15 disposed on the substrate 11.

In the solution detector of the present embodiment, the substrate 11 may comprise a first region R1 and a second region R2, the first region R1 is a region contacting a solution to be detected, and the second region R2 is a region outside the first region R1 and not contacting the solution to be detected. Herein, the first light detecting element 12, the pH value sensing module 13, the first temperature sensing unit 14 and the electrical conductivity sensing module 15 are disposed in the first region R1. In another embodiment of the present disclosure, the first region R1 may be referred to the surfaces of electrodes contacting the solution to be detected, and the second region R2 is the region outside the first region R1; but the present disclosure is not limited thereto.

As shown in FIG. 1, the solution detector of the present embodiment may selectively further comprise a second light detecting element 16 disposed in the second region R2 of the substrate 11. In addition, the solution detector of the present embodiment may selectively further comprise a second temperature sensing unit 17 disposed in the second region R2 of the substrate 11. Herein, the second light detecting element 16 or the second temperature sensing unit 17 may comprise a transistor, but the present disclosure is not limited thereto.

In the solution detector of the present embodiment, plural conductive lines 18 and plural conductive pads 20 are also disposed on the substrate 11. The conductive lines 18 are respectively electrically connected to the conductive pads 20, and the conductive lines 18 are further respectively electrically connected to the first light detecting element 12, the pH value sensing module 13, the first temperature sensing unit 14, the electrical conductivity sensing module 15, the second light detecting element 16 and the second temperature sensing unit 17. The solution detector can be electrically connected to an external device through the conductive pads 20, so the external device can drive the solution detector or a signal detected by the solution detector can be transmitted to the external device. In addition, the position of the conductive lines 18 shown in FIG. 1 is one embodiment of the present disclosure. In another embodiment of the present disclosure, the conductive lines 18 can be disposed around the working electrode 131 or the reference electrode 132, or disposed in another manner according to the need. Similarly, the positions of the working electrode 131, the reference electrode 132, the first temperature sensing unit 14 and the electrical conductivity sensing module 15 shown in FIG. 1 is also one embodiment of the present disclosure, and can be modified according to the need.

As shown in FIG. 1, the first light detecting element 12, the pH value sensing module 13, the first temperature sensing unit 14, and the electrical conductivity sensing module 15 are disposed in the first region R1, and the second light detecting element 16 and the second temperature sensing unit 17 are disposed in the second region R2.

When the solution detector of the present embodiment is used to measure the property of the solution to be detected, the first region R1 is immersed into the solution to be detected, and the first light detecting element 12 or the second light detecting element 16 can drive the second transistor TFT2 electrically connecting to the pH value sensing module 13 to further drive the pH value sensing module 13 to measure the pH value of the solution to be detected. In addition, the first light detecting element 12 or the second light detecting element 16 can also be used to detect the environment, for example, day or night. In another embodiment, the pH value sensing module 13 can also be driven by an external circuit.

For example, when the solution to be detected has a certain level of transmittance, the second transistor TFT2 can be driven by the first light detecting element 12 or/and the second light detecting element 16 to further drive the pH value sensing module 13 to measure the pH value of the solution to be detected, and the brightness of the solution to be detected, the pH value of the solution to be detected and the brightness of the environment can also be recorded simultaneously. When the transmittance of the solution to be detected is too low, the second transistor TFT2 can be driven by the second light detecting element 16 to further drive the pH value sensing module 13 to measure the pH value of the solution to be detected, and the pH value of the solution to be detected and the brightness of the environment can also be recorded simultaneously. However, the present disclosure is not limited thereto.

In addition, the first temperature sensing unit 14 in the first region R1 can detect the liquid temperature of the solution to be detected, the electrical conductivity sensing module 15 in the first region R1 can measure the electrical conductivity of the solution to be detected, and the second temperature sensing unit 17 in the second region R2 can detect the temperature of the environment of the solution to be detected.

Directions X, Y and Z are indicated in FIG. 1. The direction Z can be a normal direction of an upper surface of the substrate 11. The direction Z can be perpendicular to the directions X and Y, and the direction X can be perpendicular to the direction Y. Hereinafter, the following embodiments and figures are describes based on the directions X, Y and Z.

Figure 2:
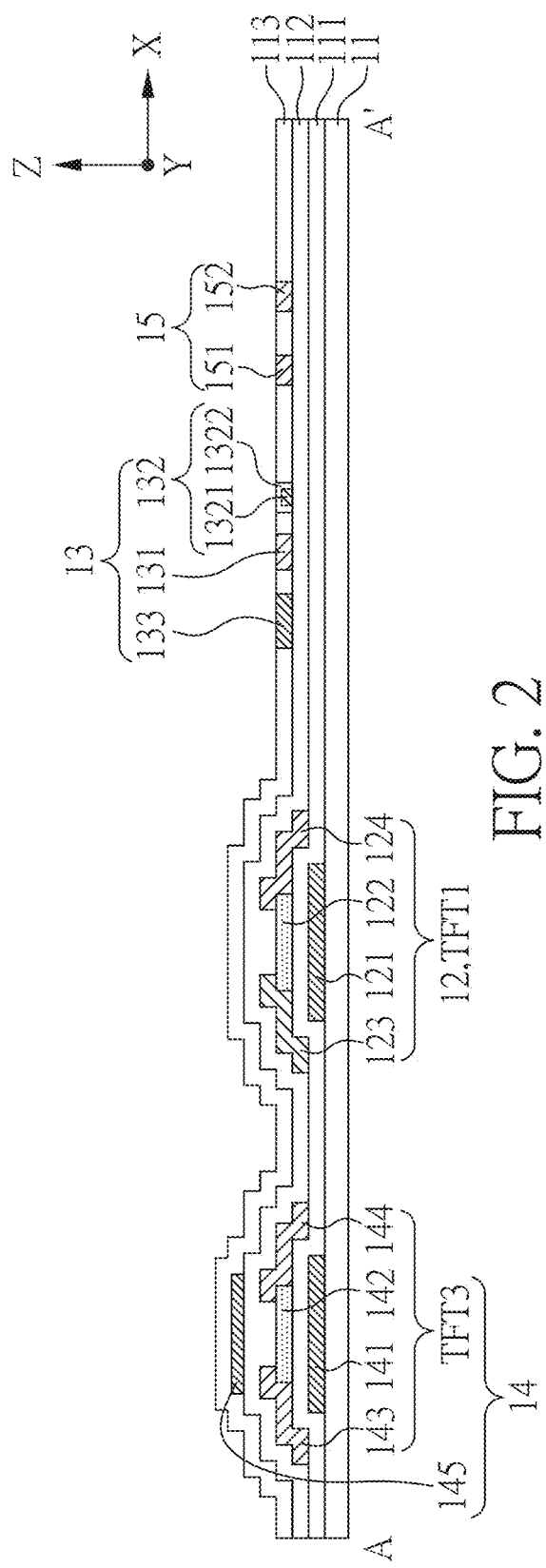
FIG. 2 is a cross-sectional schematic view of FIG. 1 along a line A-A'.
Figure 3:
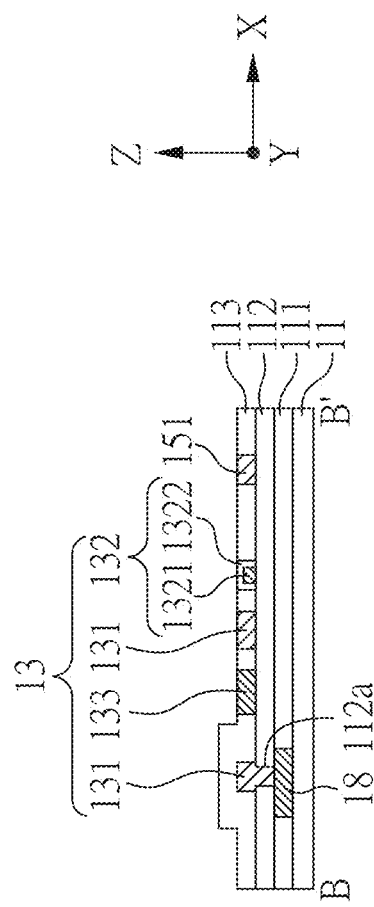
FIG. 3 is a cross-sectional schematic view of FIG. 1 along a line B-B'.

FIG. 2 to FIG. 4 are cross-sectional schematic views of FIG. 1. More specifically, FIG. 2 is a cross-sectional schematic view of FIG. 1 along a line A-A', FIG. 3 is a cross-sectional schematic view of FIG. 1 along a line B-B', and FIG. 4 is a cross-sectional schematic view of FIG. 1 along a line C-C'.

The solution detector of the present embodiment is manufactured by the technique and process of the transistor. As shown in FIG. 2 to FIG. 4, a substrate 11 is provided, wherein the substrate 11 may be a non-flexible substrate, a flexible substrate, a thin film or a combination thereof. The material of the substrate 11 may include quartz, glass, silicon wafer, sapphire, polycarbonate (PC), polyimide (PI), polypropylene (PP), polyethylene terephthalate (PET) or other plastic or polymer material, or a combination thereof, but the present disclosure is not limited thereto. When the substrate 11 is a thin film, which may be a water barrier film or an encapsulating film formed by laminated inorganic-organic-inorganic (I-O-I) insulating layers.

A first metal layer is formed on the substrate 11. The first metal layer includes a first gate electrode 121, a second gate electrode 191, a third gate electrode 141 and a fourth gate electrode 161, and further includes conductive lines 18. Herein, the material of the first metal layer may comprises, but is not limited to, copper (Cu), aluminum (Al), molybdenum (Mo), tungsten (W), gold (Au), chromium (Cr), nickel (Ni), platinum (Pt), titanium (Ti), Cu alloy, Al alloy, Mo alloy, W alloy, Au alloy, Cr alloy, Ni alloy, Pt alloy, Ti alloy, other suitable metal, a combination thereof, or other conductive material with good conductivity or small resistance. Herein, the first metal layer may have a single-layered or multi-layered structure.

Then, a gate insulating layer 111 is formed on the first metal layer. The material of the gate insulating layer 111 may comprise, but is not limited to, silicon oxide, silicon nitride, silicon oxynitride, aluminum oxide, resin, polymer, photoresist, or a combination thereof. In one embodiment of the present disclosure, the material of the gate insulating layer 111 includes silicon nitride, but the present disclosure is not limited thereto.

Next, a first active layer 122, a second active layer 192, a third active layer 142 and a fourth active layer 162 are formed on the gate insulating layer 111, wherein the first active layer 122 is disposed corresponding to the first gate electrode 121, the second active layer 192 is disposed corresponding to the second gate electrode 191, the third active layer 142 is disposed corresponding to the third gate electrode 141, and the fourth active layer 162 is disposed corresponding to the fourth gate electrode 161. Herein, the first active layer 122, the second active layer 192, the third active layer 142 and the fourth active layer 162 may respectively include amorphous silicon, polycrystalline-silicon such as low temperature polycrystalline-silicon (LTPS), or metal oxide such as IGZO (indium gallium zinc oxide), AIZO (aluminum indium zinc oxide), HIZO (hafnium indium zinc oxide), ITZO (indium tin zinc oxide), IGZTO (indium gallium zinc tin oxide), or IGTO (indium gallium tin oxide), but the present disclosure is not limited thereto.

In one embodiment of the present disclosure, the first active layer 122, the second active layer 192, the third active layer 142 and the fourth active layer 162 respectively comprise amorphous silicon, but the present disclosure is not limited thereto.

Then, a second metal layer is formed on the first active layer 122, the second active layer 192, the third active layer 142 and the fourth active layer 162. The second metal layer comprises: a first source electrode 123, a first drain electrode 124, a second source electrode 193, a second drain electrode 194, a third source electrode 143, a third drain electrode 144, a fourth source electrode 163 and a fourth drain electrode 164. The first source electrode 123 and the first drain electrode 124 are electrically connected to the first active layer 122. The second source electrode 193 and the second drain electrode 194 are electrically connected to the second active layer 192. The third source electrode 143 and the third drain electrode 144 are electrically connected to the third active layer 142. The fourth source electrode 163 and the fourth drain electrode 164 are electrically connected to the fourth active layer 162. Herein, the material of the second metal layer may comprise, but is not limited to, Cu, Al, Mo, W, Au, Cr, Ni, Pt, Ti, Cu alloy, Al alloy, Mo alloy, W alloy, Au alloy, Cr alloy, Ni alloy, Pt alloy, Ti alloy, other suitable metal, a combination thereof, or other conductive material with good conductivity or small resistance. In addition, the second metal layer may have a single-layered or multi-layered structure.

Thus, a first transistor TFT1, a second transistor TFT2, a third transistor TFT3 and a fourth transistor TFT4 of the solution detector of the present embodiment are obtained. The first transistor TFT1 comprises: the first gate electrode 121; a part of the gate insulating layer 111 disposed on the first gate electrode 121; the first active layer 122 disposed on the gate insulating layer 111 and corresponding to the first gate electrode 121; and the first source electrode 123 and the first drain electrode 124 disposed on the first active layer 122 and electrically connected to the first active layer 122. The second transistor TFT2 comprises: the second gate electrode 191; a part of the gate insulating layer 111 disposed on the second gate electrode 191; the second active layer 192 disposed on the gate insulating layer 111 and corresponding to the second gate electrode 191; and the second source electrode 193 and the second drain electrode 194 disposed on the second active layer 192 and electrically connected to the second active layer 192. The third transistor TFT3 comprises: the third gate electrode 141; a part of the gate insulating layer 111 disposed on the third gate electrode 141; the third active layer 142 disposed on the gate insulating layer 111 and corresponding to the third gate electrode 141; and the third source electrode 143 and the third drain electrode 144 disposed on the third active layer 142 and electrically connected to the third active layer 142. The fourth transistor TFT4 comprises: the fourth gate electrode 161; a part of the gate insulating layer 111 disposed on the fourth gate electrode 161; the fourth active layer 162 disposed on the gate insulating layer 111 and corresponding to the fourth gate electrode 161; and the fourth source electrode 163 and the fourth drain electrode 164 disposed on the fourth active layer 162 and electrically connected to the fourth active layer 162.

In the present embodiment, the first transistor TFT1, the second transistor TFT2, the third transistor TFT3 and the fourth transistor TFT4 are bottom gate transistors, but the present disclosure is not limited thereto. In another embodiment of the present disclosure, at least one of the first transistor TFT1, the second transistor TFT2, the third transistor TFT3 and the fourth transistor TFT4 can be a top gate transistor. In addition, in the present disclosure, the positions of the first transistor TFT1, the second transistor TFT2, the third transistor TFT3 and the fourth transistor TFT4 are not limited to the positions shown in FIG. 1, and can be adjusted based on the design. Furthermore, in the present embodiment, the first transistor TFT1, the second transistor TFT2, the third transistor TFT3 and the fourth transistor TFT4 can be selectively electrically connected to each other in series or in parallel, based on the design.

Even though the structure and the preparation method of the transistor of the second temperature sensing unit 17 (as shown in FIG. 1) are not described in the aforesaid description, the structure and the preparation method of the transistor of the second temperature sensing unit 17 can be similar to those of the first transistor TFT1, the second transistor TFT2, the third transistor TFT3 and the fourth transistor TFT4, and are not repeated again.

Then, as shown in FIG. 2 to FIG. 4, a first insulating layer 112 is formed on the first transistor TFT1, the second transistor TFT2, the third transistor TFT3 and the fourth transistor TFT4. The material of the first insulating layer 112 may comprise, but is not limited to, silicon oxide, silicon oxynitride, silicon nitride, aluminum oxide, resin, polymer, photoresist, or a combination thereof. In one embodiment of the present disclosure, the material of the first insulating layer 112 comprises silicon nitride, but the present disclosure is not limited thereto. Thus, the solution detector of the present embodiment further comprises a first insulating layer 112, which is disposed on the gate insulating layer 111 and the second metal layer.

After forming the first insulating layer 112, a light shielding layer 145 is formed, and the light shielding layer 145 and the third transistor TFT3 are at least partially overlapped. More specifically, the light shielding layer 145 and the third active layer 142 of the third transistor TFT3 are at least partially overlapped. Thus, in the present embodiment, the first temperature sensing unit 14 comprises the third transistor TFT3 and the light shielding layer 145. Since the light shielding layer 145 and the third active layer 142 are overlapped, the light influence from the upper side of the third active layer 142 can be blocked by the light shielding layer 145. Meanwhile, the third active layer 142 and the third gate electrode 141 are overlapped, the light influence from the bottom side of the third active layer 142 can also be blocked by the third gate electrode 141. Thus, when using the solution detector of the present embodiment, the carrier transportation in the third active layer 142 is mainly related to the temperature of the solution to be detected, and the light influence on the carrier transportation in the third active layer 142 can be reduced due to the shielding of the light shielding layer 145 and the third gate electrode 141. Thus, the third transistor TFT3 can mainly measure the temperature of the solution, and the sensitivity of the third transistor TFT3 for measuring the temperature of the solution can be improved. In the present embodiment, the material of the light shielding layer 145 may comprise a metal, a black matrix or a combination thereof. Examples of the metal may comprise, but are not limited to, chromium (Cr), nickel (Ni), silver (Ag), aluminum (Al), titanium (Ti), molybdenum (Mo), other metal capable of reflecting light or absorbing light, or a combination thereof. In addition, when the light shielding layer 145 is a metal layer, the light shielding layer 145 can be a single-layered or a multi-layered metal layer. In one embodiment of the present disclosure, the light shielding layer 145 is a Ti/Al/Ti triple-layered metal layer. In another embodiment of the present disclosure, the light shielding layer 145 is a Mo/Al/Mo triple-layered metal layer. However, the present disclosure is not limited thereto.

After forming the first insulating layer 112, a working electrode 131 is formed, which is disposed on the first insulating layer 112. In addition, as shown in FIG. 3, the first insulating layer 112 may further comprise a contact via 112a, and the working electrode 131 is electrically connected to the conductive line 18 through the contact via 112a. In the present embodiment, the material of the working electrode 131 may comprise a metal, a conductive metal oxide, a combination thereof or other suitable electrode material. Examples of the metal include, but are not limited to, Cu, Ni, Au, Ag, Al, Ti, Cr, Mo, metal alloy or a combination thereof. Examples of the conductive metal oxide include, but are not limited to, ITO (indium tin oxide), IZO (indium zinc oxide), ITZO (indium tin zinc oxide), IGZO (indium gallium zinc oxide) or AZO (aluminum zinc oxide, AZO). In one embodiment of the present disclosure, the material of the working electrode 131 is ITO. In another embodiment of the present disclosure, the material of the working electrode 131 is Ag or Au. However, the present disclosure is not limited thereto. In addition, a thickness of the working electrode 131 may be, for example, ranged from about 2500 Å to about 10000 Å, so the stability of the pH value sensing module 13 can be improved, and the process stability can also be improved.

After forming the first insulating layer 112, a first electrode 151 and a second electrode 152 of the electrical conductivity sensing module 15 is further formed. Similarly, even not shown in the figure, the first electrode 151 and the second electrode 152 of the electrical conductivity sensing module 15 can also be electrically connected to the conductive lines 18 through other contact vias of the first insulating layer 112. Herein, the material of the first electrode 151 and the second electrode 152 can be identical to or different from the material of the working electrode 131. In one embodiment of the present disclosure, the materials of the first electrode 151 and the second electrode 152 are ITO, but the present disclosure is not limited thereto.

After forming the first insulating layer 112, a reference electrode 132 is further formed. Similarly, even not shown in the figure, the reference electrode 132 can also be electrically connected to the conductive line 18 through another contact via of the first insulating layer 112. Herein, the reference electrode 132 comprises an inner electrode layer 1321 and an outer electrode layer 1322. The material of the inner electrode layer 1321 comprises Ag, and the material of the outer electrode layer 1322 comprises AgCl, $Ag_2O$ or a combination thereof. Herein, an Ag layer (as the inner electrode layer 1321) is firstly deposited, and then an electroplating process or a solution process (for example, the Ag layer is immersed into a $FeCl_3$ solution for a period of time to let Ag convert into AgCl through a redox reaction) is performed to form a thin layer of an AgCl layer (as the outer electrode layer 1322) to obtain the reference electrode 132. In addition, a thickness of the inner electrode layer 1321 can be ranged from about 500 Å to about 8000 Å, and a thickness of the outer electrode layer 1322 can be ranged from about 1000 Å to about 6000 Å. In some embodiments, a ratio of the thickness of the outer electrode layer 1322 in the direction Z to the thickness of the reference electrode 132 in the direction Z can be ranged from about 20% to about 80%, but the present disclosure is not limited thereto.

After forming the first insulating layer 112, a counter electrode 133 is further formed. Similarly, even not shown in the figure, the counter electrode 133 can also be electrically connected to the conductive line 18 through another contact via of the first insulating layer 112. Herein, the material of the counter electrode 133 may comprise silver (Ag), gold (Au), platinum (Pt) or a combination thereof. In addition, a thickness of the counter electrode 133 can be ranged from about 5000 Å to about 10000 Å.

Before forming the reference electrode 132 or the counter electrode 133, a buffer layer (not shown in the figure) can be selectively formed on the first insulating layer 112 to further improve the adhesion of the material of the reference electrode 132 or the counter electrode 133 sequentially formed. The material of the buffer layer may comprise Ti, Cr, Ni or other suitable metal, or a combination thereof, but the present disclosure is not limited thereto.

After the aforesaid process, the pH value sensing module 13 of the solution detector of the present embodiment is obtained. As shown in FIG. 1 and FIG. 2, the pH value sensing module 13 of the present embodiment is adjacent to the first light detecting element 12 but electrically isolated from the first light detecting element 12. Herein, the pH value sensing module 13 of the present embodiment comprises the working electrode 131, the reference electrode 132 and the counter electrode 133, and the working electrode 131 is disposed between the reference electrode 132 and the counter electrode 133. More specifically, the working electrode 131 is adjacent to the reference electrode 132 but electrically isolated from the reference electrode 132, and the counter electrode 133 is also adjacent to the working electrode 131 but electrically isolated from the working electrode 131. In some embodiments, areas of the working electrode 131, the reference electrode 132 and the counter electrode 133 can be different. For example, the area of the counter electrode 133 can be greater than the area of the working electrode 131, and the area of the working electrode 131 can be greater than the area of the reference electrode 132. Furthermore, a sheet resistance of the counter electrode 133 can be less than a sheet resistance of the working electrode 131. For example, the material of the counter electrode 133 may comprise Ag, and the material of the working electrode 131 may comprise ITO or other conductive metal oxide. In this case, more hydrogen ions can be adsorbed on the working electrode 131 when the working electrode 131 contacts the solution to be detected to further improve the sensitivity of the pH value sensing module 13. However, the present disclosure is not limited thereto. In other embodiments, the pH value sensing module 13 may not comprise the counter electrode 133.

As shown in FIG. 2 to FIG. 4, a second insulating layer 113 is formed after forming the light shielding layer 145, the pH value sensing module 13 and the electrical conductivity sensing module 15. The second insulating layer 113 covers the first transistor TFT1, the second transistor TFT2, the third transistor TFT3 and the fourth transistor TFT4, and further covers the light shielding layer 145 and the conductive lines 18. In addition, even not shown in the figure, the second insulating layer 113 also covers the transistor of the second temperature sensing unit 17 (as shown in FIG. 1). Herein, the material of the second insulating layer 113 may comprise, but is not limited to, silicon oxide, silicon nitride, silicon oxynitride, aluminum oxide, resin, polymer, photoresist, or a combination thereof.

Then, as shown in FIG. 2 and FIG. 3, the second insulating layer 113 on at least a part of the surfaces of the working electrode 131, the reference electrode 132, the counter electrode 133, the first electrode 151 and the second electrode 152 is removed to expose at least a part of the surfaces of the working electrode 131, the reference electrode 132, the counter electrode 133, the first electrode 151 and the second electrode 152. In one embodiment of the present disclosure, the whole surfaces of the working electrode 131, the reference electrode 132, the counter electrode 133, the first electrode 151 and the second electrode 152 are exposed from the second insulating layer 113. In other embodiments of the present disclosure, the second insulating layer 113 partially covers at least one of the surfaces of the working electrode 131, the reference electrode 132, the counter electrode 133, the first electrode 151 and the second electrode 152, for example, partially covers the surface of the electrode near to the edge of the electrode. Thus, the problem of the peeling of the electrode can be improved. For example, as shown in FIG. 1 and FIG. 3, a part of the surface of the working electrode 131 is covered by the second insulating layer 113, but the present disclosure is not limited thereto. In other embodiments of the present disclosure, the whole surface of the working electrode 131 may not be covered by the second insulating layer 113.

As mentioned above, in the preparation of the solution detector of the present embodiment, after forming the first insulating layer 112, the light shielding layer 145 is prepared in another step different from the step for preparing the reference electrode 132 and the counter electrode 133. However, in another embodiment of the present disclosure, when the light shielding layer 145, the reference electrode 132 and the counter electrode 133 are formed by the same material (for example, including Ag), the shielding layer 145, the reference electrode 132 and the counter electrode 133 can be formed in the same step.

In addition, as mentioned above, in the preparation of the solution detector of the present embodiment, after forming the first insulating layer 112, the second insulating layer 113 is formed after forming the pH value sensing module 13 and the electrical conductivity sensing module 15. However, in other embodiments of the present disclosure, the second insulating layer 113 can be formed in advance, and then the pH value sensing module 13 and the electrical conductivity sensing module 15 are formed after patterning the second insulating layer 113.

Furthermore, in the present disclosure, the orders for forming the working electrode 131, the reference electrode 132 and the counter electrode 133 of the pH value sensing module 13 as well as the first electrode 151 and the second electrode 152 of the electrical conductivity sensing module 15 are not particularly limited.

FIG. 5 is a cross-sectional schematic view of FIG. 1 along a line C-C' according to another embodiment of the present disclosure. The cross-sectional schematic view of the solution detector of the present embodiment is similar to that shown in FIG. 4, except that the conductive lines 18 in FIG. 4 is formed by the first metal layer (including the second gate electrode 191 and the fourth gate electrode 161), but the conductive lines 18 in FIG. 5 is formed by the second metal layer (including the second source electrode 193, the second drain electrode 194, the fourth source electrode 163 and the fourth drain electrode 164).

Figure 6:
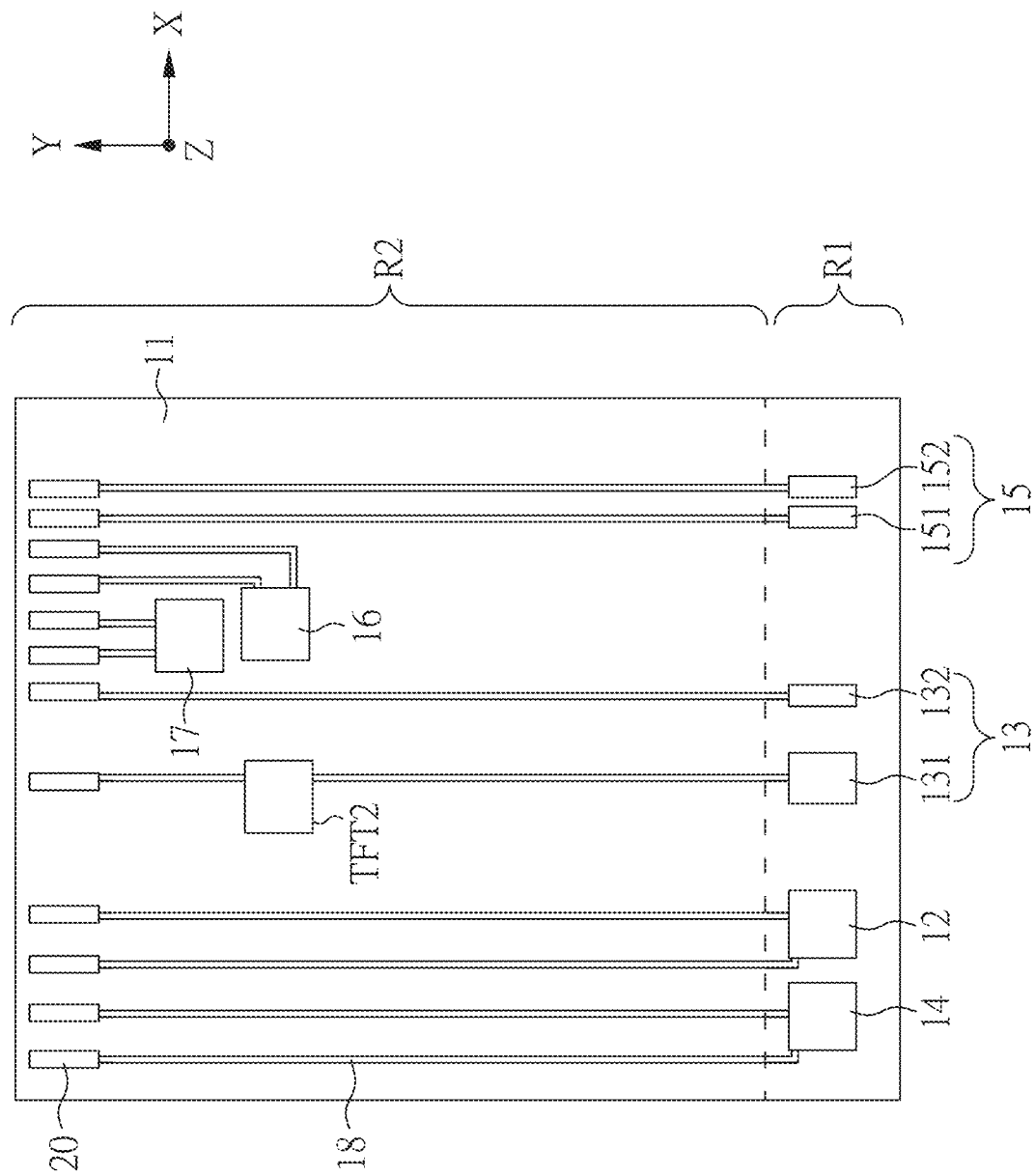
FIG. 6 is a top schematic view of a solution detector according to another embodiment of the present disclosure.

FIG. 6 is a top schematic view of a solution detector according to another embodiment of the present disclosure. The solution detector of the present embodiment is similar to that shown in FIG. 1, except that the solution detector of the present embodiment does not include the counter electrode 133 shown in FIG. 1.

Figure 7:
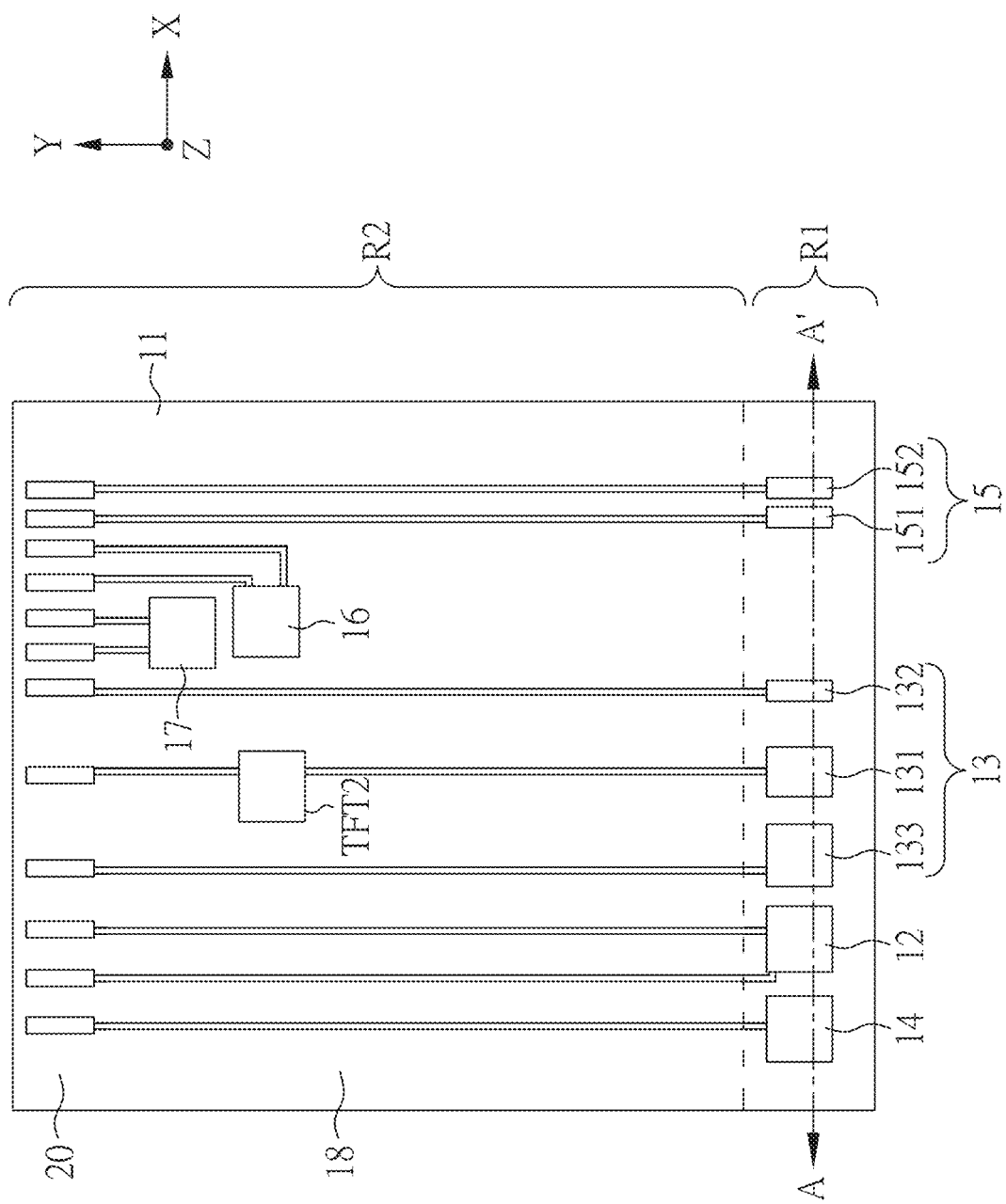
FIG. 7 is a top schematic view of a solution detector according to further another embodiment of the present disclosure.
Figure 8:
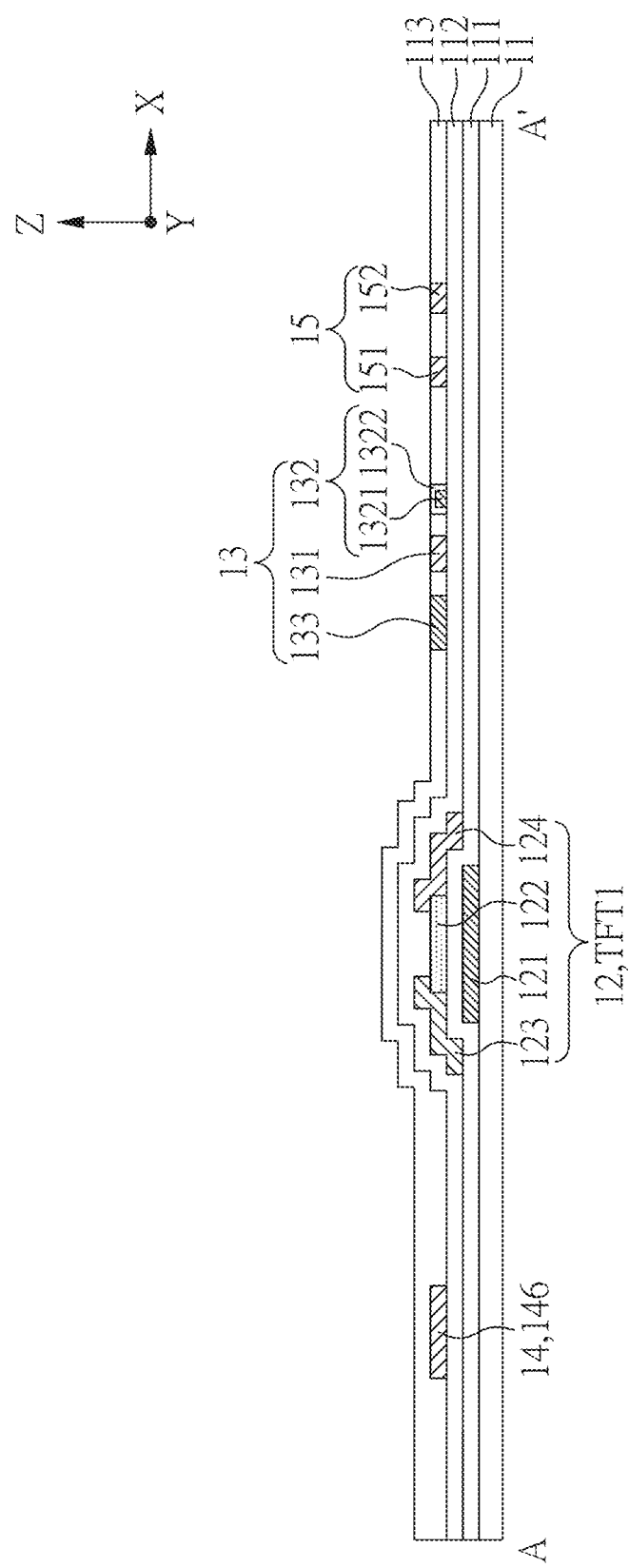
FIG. 8 is a cross-sectional schematic view of FIG. 7 along a line A-A'.

FIG. 7 is a top schematic view of a solution detector according to further another embodiment of the present disclosure, and FIG. 8 is a cross-sectional schematic view of FIG. 7 along a line A-A'. The solution detector of the present embodiment is similar to that shown in FIG. 1 and FIG. 2, except that the first temperature sensing unit 14 of the solution detector of the present embodiment is different from that shown in FIG. 1. In the present embodiment, the first temperature sensing unit 14 comprises a temperature resistance 146, and the material of the temperature resistance 146 can be ITO.

As mentioned above, the present disclosure provides a solution detector, which is prepared by the process for preparing transistors. Thus, the solution detector of the present disclosure is a low cost and stable solution detector. In addition, the solution detector of the present disclosure can be used to detect the basic properties (such as pH value, temperature and electrical conductivity) of the aqueous solution, and thus can be applied to the distributed water monitoring systems with low cost. For example, the solution detector of the present disclosure can be applied to various fields such as distributed smart culture systems, detections of wastewater discharge without permission into river, smart water meters, and toilets for care or urine detection for elderly people or children, to achieve the purpose of distributed detections. In addition, if the solution detector of the present disclosure is used along with the cloud connection, a water interconnected system such as AirBox can be accomplished.

In the present disclosure, the features in different embodiments of the present disclosure can be mixed to form another embodiment without departing from the spirit and scope of the disclosure as hereinafter claimed.

Although the present disclosure has been explained in relation to its embodiment, it is to be understood that many other possible modifications and variations can be made without departing from the spirit and scope of the disclosure as hereinafter claimed.

What is claimed is:

1. A solution detector, comprising:
   a substrate;
   a first light detecting element disposed on the substrate and comprising a first transistor;
   a pH value sensing module disposed on the substrate and comprising a working electrode and a reference electrode; and
   a first temperature sensing unit disposed on the substrate, wherein the first temperature sensing unit comprises a third transistor and a light shielding layer, and the light shielding layer and the third transistor are at least partially overlapped.

2. The solution detector of claim 1, further comprising a first insulating layer, wherein the first transistor comprises a first gate electrode, the first insulating layer is disposed on the first gate electrode, and the working electrode is disposed on the first insulating layer.

3. The solution detector of claim 1, wherein the working electrode is electrically connected to a second transistor.

4. The solution detector of claim 3, further comprising a second insulating layer, wherein the second insulating layer covers the second transistor.

5. The solution detector of claim 1, wherein the first temperature sensing unit comprises a temperature resistance.

6. The solution detector of claim 1, wherein the third transistor comprises an active layer, and the light shielding layer and the active layer are overlapped.

7. The solution detector of claim 1, wherein a material of the working electrode comprises a metal, a conductive metal oxide or a combination thereof.

8. The solution detector of claim 1, wherein a material of the reference electrode comprises silver.

9. The solution detector of claim 8, wherein the material of the reference electrode further comprises AgCl, $Ag_2O$ or a combination thereof.

10. The solution detector of claim 1, wherein the pH value sensing module further comprises a counter electrode.

11. The solution detector of claim 10, wherein an area of the counter electrode is greater than an area of the working electrode, and the area of the working electrode is greater than an area of the reference electrode.

12. The solution detector of claim 10, wherein the working electrode is disposed between the reference electrode and the counter electrode.

13. The solution detector of claim 10, wherein a sheet resistance of the counter electrode is less than a sheet resistance of the working electrode.

14. The solution detector of claim 1, wherein the substrate comprises a first region, the first region is a region contacting a solution to be detected, and the first light detecting element and the pH value sensing module are disposed in the first region.

15. The solution detector of claim 14, further comprising a second light detecting element, wherein the substrate further comprises a second region, the second region is a region outside the first region, and the second light detecting element is disposed in the second region.

16. The solution detector of claim 14, further comprising a second temperature sensing unit, wherein the substrate further comprises a second region, the second region is a region outside the first region, and the second temperature sensing unit is disposed in the second region.

17. The solution detector of claim 1, further comprising an electrical conductivity sensing module disposed on the substrate.

* * * * *